(12) United States Patent
Malhotra et al.

(10) Patent No.: US 10,940,274 B2
(45) Date of Patent: Mar. 9, 2021

(54) NASAL SPRAY ASSEMBLY

(71) Applicant: CIPLA LIMITED, Mumbai (IN)

(72) Inventors: Geena Malhotra, Mumbai (IN);
Dinakaran Govindasamy, Bangalore (IN)

(73) Assignee: CIPLA LIMITED, Mumbai (IN)

( * ) Notice: Subject to any disclaimer, the term of this patent is extended or adjusted under 35 U.S.C. 154(b) by 327 days.

(21) Appl. No.: 15/780,583

(22) PCT Filed: Dec. 1, 2016

(86) PCT No.: PCT/IN2016/050427
§ 371 (c)(1),
(2) Date: May 31, 2018

(87) PCT Pub. No.: WO2017/094027
PCT Pub. Date: Jun. 8, 2017

(65) Prior Publication Data
US 2018/0361085 A1  Dec. 20, 2018

(30) Foreign Application Priority Data

Dec. 1, 2015 (IN) .......................... 4522/MUM/2015

(51) Int. Cl.
*A61M 11/00* (2006.01)
*A61M 15/08* (2006.01)
(Continued)

(52) U.S. Cl.
CPC ........ *A61M 11/007* (2014.02); *A61M 15/004* (2014.02); *A61M 15/0036* (2014.02);
(Continued)

(58) Field of Classification Search
CPC .. A61M 11/00; A61M 11/006; A61M 11/007; A61M 11/008; A61M 11/06;
(Continued)

(56) References Cited

U.S. PATENT DOCUMENTS 3,906,950 A 9/1975 Cocozza
5,433,343 A 7/1995 Meshberg
(Continued)

FOREIGN PATENT DOCUMENTS

| EP | 0311863 B | 1/1993 |
|---|---|---|
| WO | 9115303 A2 | 10/1991 |
| WO | 2012119153 A2 | 9/2012 |

*Primary Examiner* — Colin W Stuart
(74) *Attorney, Agent, or Firm* — Maschoff Brennan (57) ABSTRACT

A nasal spray assembly for administering a medicament to the nose of a user includes a nasal device and a container that has a reservoir containing the medicament. The reservoir is sealed by a movable piston. The nasal device includes a body, a cap that defines a socket into which the body can be inserted, an outlet, and a piercing element. The piercing element includes a piercer inlet and extends into the socket from a piercer stop within the socket. The nasal spray assembly is arranged such that, as the body is moved into the socket along a first axis, the piercing element pierces and passes through the piston such that the piercer inlet lies within the reservoir, contact between the piercer stop and piston forces the piston into the container, reducing the reservoir volume and forcing medicament from the reservoir through the conduit and out of the outlet.

18 Claims, 3 Drawing Sheets

(51) Int. Cl.
*A61M 15/00* (2006.01)
*B05B 11/02* (2006.01)

(52) U.S. Cl.
CPC .............. *A61M 15/08* (2013.01); *B05B 11/02* (2013.01); *A61M 2205/273* (2013.01)

(58) Field of Classification Search
CPC .............. A61M 15/00; A61M 15/0001; A61M 15/0028; A61M 15/003; A61M 15/0033; A61M 15/0035; A61M 15/0036; A61M 15/0038; A61M 15/004; A61M 15/0041; A61M 15/08; A61M 15/085; A61M 2205/07; A61M 2205/071; A61M 2205/073; A61M 2205/276; A61M 2205/273; A61M 2205/27; B05B 11/02
See application file for complete search history.

(56) References Cited

U.S. PATENT DOCUMENTS

| | | | |
|---|---|---|---|
| 6,109,479 A | 8/2000 | Ruckdeschel | |
| 6,173,868 B1* | 1/2001 | DeJonge | A61M 15/0065 222/153.13 |
| 6,382,465 B1* | 5/2002 | Greiner-Perth | A61M 15/0065 222/309 |
| 6,708,846 B1 | 3/2004 | Fuchs et al. | |
| 6,887,672 B2* | 5/2005 | Weber | C07K 14/70535 435/7.1 |
| 8,734,392 B2* | 5/2014 | Stadelhofer | A61M 15/0028 128/200.14 |
| 9,555,950 B2* | 1/2017 | Le Maner | B05B 11/308 |
| 9,861,770 B2* | 1/2018 | Vogt | A61M 11/007 |
| 2006/0039869 A1 | 2/2006 | Wermeling et al. | |
| 2008/0210229 A1 | 9/2008 | Corbacho | |
| 2010/0095957 A1* | 4/2010 | Corbacho | A61M 15/0035 128/200.14 |
| 2014/0060523 A1* | 3/2014 | Sogaro | B05B 1/34 128/200.14 |
| 2015/0005356 A1 | 1/2015 | Flemin | |
| 2015/0258019 A1 | 9/2015 | Crystal et al. | |

* cited by examiner

NASAL SPRAY ASSEMBLY

FIELD OF INVENTION

The present invention relates to a nasal spray assembly for delivering medicament to a user, the nasal spray assembly comprising a nasal device and a medicament container. The invention also relates to a nasal device used to form the nasal spray assembly and to a method of preparing and using such nasal spray assembly.

BACKGROUND & PRIOR ART

The use of nasal sprays to deliver a medicament to the nose and/or nasal cavity of a user is well known and there have been many devices adapted for such use. Spray bottle devices, for example squeezable bottles with a spray nozzle can be used to deliver a fine spray of liquid up the nose, but accurate dosing using such devices can be difficult due to the differences in the ability of different users to squeeze the bottle.

A single dose nasal delivery device is disclosed in EP0311863 in which a nasal spray assembly is disclosed which uses a piston pump defining a dosing chamber to dispense a predetermined volume of fluid. A further example of a nasal delivery device is shown is EP1071517.

Such nasal sprays may be assembled from a kit which comprises a nasal device and a container, such as a vial, of medicament to be dispensed. The container may be pre-installed in the device so that the user only needs to actuate the device.

Known nasal spray assemblies may be complicated to assemble and may be difficult for a user to handle and use correctly. Incorrect handling, or use, of a nasal spray assembly could lead to, amongst other things, wasted medicament, incorrect dosing or possibly damage to one or more components of the assembly.

OBJECT OF THE INVENTION

An object of the present invention is to provide a nasal spray assembly that provides a simple assembly of components for ease of handling.

Another object of the present invention is to provide a nasal spray assembly which is comfortable for use by a user/patient for the respective purpose thereby achieving user/patient compliance.

Yet another object of the present invention is to provide a nasal spray assembly which prevents the conventional problems of wasted medicament due to incorrect handling or use of the said assembly, incorrect dosing and/or assembly damage due to operation of the components of the assembly.

SUMMARY OF THE INVENTION

According to one aspect of the present invention, there is provided a nasal spray assembly comprising a nasal device and a container, the container including a reservoir containing a medicament, the reservoir being sealed by a movable piston, the nasal spray assembly being for administering the medicament to the nose of a user, the nasal device comprising a body and a cap, the cap defining a socket into which the body can be inserted, an outlet and a piercing element, the piercing element including a piercer inlet and extending into the socket from a piercer stop within the socket, the piercer inlet being connected to the outlet by a conduit, the body holding the container, and the nasal spray assembly being arranged such that, as the body is moved into the socket along a first axis, the piercing element pierces and passes through the piston such that the piercer inlet lies within the reservoir, contact between the piercer stop and piston causes the piston to be forced into the container, reducing the reservoir volume and thereby forcing medicament from the reservoir through the conduit and out of the outlet, the nasal spray assembly being characterised in that the body and cap cooperate to provide a pre-lock and a post-lock, the pre-lock engages automatically when the body is inserted a first predetermined distance into the socket and, when engaged, the pre-lock substantially prevents withdrawal of the body from the cap and hinders further movement of the body into the cap until at least a threshold force has been applied thereby retaining the body and cap in a pre-use configuration, the post-lock engages automatically when the body is inserted a second predetermined distance into the socket and, when engaged, substantially prevents withdrawal of the body from the cap thereby substantially retaining the body and cap in a post-use configuration, the second predetermined distance is greater than the first predetermined distance.

According to second aspect of the present invention, there is provided a nasal device comprising a body and a cap, the cap defining a socket into which the body can be inserted, an outlet and a piercing element, the piercing element including a piercer inlet and extending into the socket from a piercer stop within the socket, the piercer inlet being connected to the outlet by a conduit, the nasal device being characterised in that the body and cap cooperate to provide a pre-lock and a post-lock, the pre-lock engages automatically when the body is inserted a first predetermined distance into the socket and, when engaged, the pre-lock substantially prevents withdrawal of the body from the cap and hinders further movement of the body into the cap until at least a threshold force has been applied thereby retaining the body and cap in a pre-use configuration, the post-lock engages automatically when the body is inserted a second predetermined distance into the socket and, when engaged, substantially prevents withdrawal of the body from the cap thereby substantially retaining the body and cap in a post-use configuration, the second predetermined distance is greater than the first predetermined distance, the nasal device being suitable for use in the nasal spray assembly.

According to third aspect of the present invention, there is provided a method of using a nasal spray assembly comprising a nasal device and a container, the method comprising the steps of:
a) arranging the container in the body;
b) inserting the body into the socket of the cap by a first distance to engage the pre-lock; and
c) applying a force exceeding a threshold force to insert the body into the socket by a second predetermined distance, thereby ejecting the medicament from the reservoir from the outlet and engaging the post-lock.

According to fourth aspect of the present invention, there is provided a nasal spray assembly comprising a nasal device and a container, the container including a reservoir containing a medicament, the reservoir being sealed by a movable piston, the nasal spray assembly being for administering the medicament to the nose of a user, the nasal device comprising a body and a cap, the cap defining a socket into which the body can be inserted, an outlet and a piercing element, the piercing element including a piercer inlet and extending into the socket from a piercer stop within the socket, the piercer inlet being connected to the outlet by a conduit, the body holding the container, and the nasal spray assembly being arranged such that, as the body is moved into the socket along a first axis, the piercing element pierces and passes through the piston such that the piercer inlet lies within the reservoir, contact between the piercer stop and piston causes the piston to be forced into the container, reducing the reservoir volume and thereby forcing medicament from the reservoir through the conduit and out of the outlet, the nasal spray assembly being characterised in that the body and cap cooperate to provide a pre-lock and a post-lock, the pre-lock engages automatically when the body is inserted a first predetermined distance into the socket and, when engaged, the pre-lock substantially prevents withdrawal of the body from the cap and hinders further movement of the body into the cap until at least a threshold force has been applied thereby retaining the body and cap in a pre-use configuration, the post-lock engages automatically when the body is inserted a second predetermined distance into the socket and, when engaged, substantially prevents withdrawal of the body from the cap thereby substantially retaining the body and cap in a post-use configuration, the second predetermined distance is greater than the first predetermined distance; and the medicament comprising one or more active pharmaceutical ingredient with pharmaceutically acceptable excipients suitable for nasal delivery.

According to fifth aspect of the present invention, there is provided a method of delivering a medicament to the nose of a patient, the method comprising the steps of:
a) providing a nasal spray assembly substantially as described above, the pre lock being engaged;
b) arranging the outlet of the device in or near the nostril of a user; and
c) applying a force exceeding a threshold force to insert the body into the socket by a second predetermined distance, thereby ejecting the medicament from the reservoir from the outlet and engaging the post-lock.

BRIEF DESCRIPTION OF THE FIGURES

The present invention will now be described by way of example only with reference to the following figures in which.

Further, skilled artisans will appreciate that elements in the figures are illustrated for simplicity and may not have been necessarily been drawn to scale. Furthermore, in terms of the construction of the device, one or more components of the device may have been represented in the figures by conventional symbols, and the figures may show only those specific details that are pertinent to understanding the embodiments of the present invention so as not to obscure the figures with details that will be readily apparent to those of ordinary skill in the art having benefit of the description herein.

DETAILED DESCRIPTION OF THE INVENTION

The present invention provides a nasal spray assembly comprising a nasal device and a container, the container including a reservoir containing a medicament, the reservoir being sealed by a movable piston, the nasal spray assembly being for administering the medicament to the nose of a user, the nasal device comprising a body and a cap, the cap defining a socket into which the body can be inserted, an outlet and a piercing element, the piercing element including a piercer inlet and extending into the socket from a piercer stop within the socket, the piercer inlet being connected to the outlet by a conduit, the body holding the container, and the nasal spray assembly being arranged such that, as the body is moved into the socket along a first axis, the piercing element pierces and passes through the piston such that the piercer inlet lies within the reservoir, contact between the piercer stop and piston causes the piston to be forced into the container, reducing the reservoir volume and thereby forcing medicament from the reservoir through the conduit and out of the outlet, the nasal device being characterised in that the body and cap cooperate to provide a pre-lock and a post-lock, the pre-lock engages automatically when the body is inserted a first predetermined distance into the socket and, when engaged, the pre-lock substantially prevents withdrawal of the body from the cap and hinders further movement of the body into the cap until at least a threshold force has been applied, thereby retaining the body and cap in a pre-use configuration, the post-lock engages automatically when the body is inserted a second predetermined distance into the socket and, when engaged, substantially prevents withdrawal of the body from the cap thereby substantially retaining the body and cap in a post-use configuration, the second predetermined distance is greater than the first predetermined distance.

By providing a pre-lock the nasal spray assembly, once assembled and containing the container, cannot be readily opened by a user and so it is less likely that the container, which may be much smaller than the nasal device, could be lost, contaminated or tampered with prior to use. The pre-lock also prevents further movement of the body into the cap until a threshold force is exceeded and this can help to prevent unwanted actuation.

The use of a threshold force can also help to ensure that complete actuation of the device occurs during use as the threshold force may be significantly higher than the ongoing actuation, or delivery, force once the pre-lock has been overcome and the body is able to move further into the socket. A threshold force followed by a subsequent reduction in force during operation may result in a user being more likely to completely actuate the device in use. This can be particularly advantageous if rapid actuation is desirable to create a spray from the outlet. The threshold force can be set so that the likelihood of unwanted actuation is reduced and the chance of complete actuation is increased. The overall force required for actuation force can be set to be still within the capabilities of the anticipated user.

The inclusion of a post-lock which retains the body and cap in a post-use configuration means that after use the device is retained in a reduced volume configuration for convenience. It is also clear that the device has been used and it cannot be re-used without re-loading. A post-lock is particularly suitable for a device intended for singe use only as the device is not intended to be re-loadable and there is no need to be able to unlock the pre- and post-locks. In such cases the pre- and/or post locks may be substantially unreleasable.

Thus a device which includes both a pre-lock and a post-lock offers considerable usability advantages for a user.

It should be noted that a nasal spray assembly is used as a broad term for any nasal delivery device which ejects medicament from an outlet. That medicament ejection could be a powder, liquid or gas wherein the medicament may comprise one or more active ingredients with pharmaceutically acceptable excipients. The ejection could take the form of a continuous stream, or a plurality of individual particulates or droplets, or a combination of the two.

A nasal device is intended to refer to any device suitable for delivery of a medicament, wherein the medicament may comprise one or more active ingredients with pharmaceutically acceptable excipients, to the nose, or up the nose, of a user to reach, for example the nasal cavity or an interior of a nostril. The device may include a delivery portion adapted for insertion up one, or both, nostrils of a user. The outlet may be located at an end of such a delivery portion. The outlet may be a spray outlet.

The container may be any suitable container for a medicament to be delivered. The container may be substantially cylindrical with a closed base and an open end. The open end may be closed by the piston to define the reservoir in which the medicament is stored. The medicament may be any flowable material, but is preferably a liquid. It should be understood that the medicament may be a powder which can be entrained in a gas, for example air, in order to flow from the container. The medicament may be in the form of a fluid, particularly a liquid. The liquid may comprise a solution, suspension or other flowable form. The reservoir may contain a volume that provides at least one dose of said medicament or a part of one dose such that administration of a predetermined number of containers makes up one dose. The container may be fabricated from any suitable material, for example a plastic or a glass. The piston may comprise, for example, a rubber, silicone or similar suitable material such that a peripheral edge of the piston forms a seal with the wall of the container so that as the piston is moved within the container the volume of the reservoir is altered. A rubber, silicone or similar resiliently deformable material may also provide a piston which can be readily pierced by a suitable piercing element. In an alternative embodiment, the piston may for a top of the container and be forced into the container, and thereby reduce the volume of the reservoir, by collapsing the walls of the container so that the piston is forced towards a base of the container.

In the pre-use configuration the piercing element may not be in contact with, or have pierced the piston. In the pre-use configuration the container may be substantially contained within the nasal device and/or a user may be substantially prevented from accessing the container.

In the post-use configuration the piercing element has pierced the piston and the medicament has been dispensed. In the post use configuration movement of the body may be substantially prevented by the post-lock alone, or a combination of the post lock and an end wall, the end wall may form an end stop for the insertion of the body into the socket. The prevention of such movement reduces the chances of any remaining medicament within the container being accidentally dispensed and also prevents unwanted rattling of the body within the cap.

The pre-lock or the post-lock may comprise a first cap shoulder carried by the cap and a first body shoulder carried by the body. The cap and body shoulders may be aligned along the first axis and may be readily pass one another during inserting of the body into the cap. At least one of these first cap and body shoulders may be being resiliently displaceable from a rest position to move past the other as the body enters the cap. Such movement facilitates the passing of the two shoulders. Once the shoulders have passed one another during insertion of the body into the cap the first cap and body shoulders may cooperate in the rest position to substantially prevent withdrawal of the body from the cap. This arrangement essentially provides a one-way snap-fit type arrangement in which in a rest position the cap and body shoulders are unable to pass one another but at least one, possibly both, of the shoulders is resiliently movable to allow the shoulders to pass one another as the body is inserted into the cap. The, or each, shoulder may then substantially return to their rest positions, or at least be biased towards them, and subsequently cooperate to prevent withdrawal of the body from the cap.

The post-lock may comprise the first cap and body shoulders and the pre-lock may comprise a second cap shoulder carried by the cap and a second body shoulder carried by the body. At least one of the second cap and body shoulders may be resiliently displaceable from a rest position to move past the other as the body enters the cap and the second shoulders cooperating in the rest position to substantially prevent withdrawal of the body from the cap. Again, this provides a one-way snap-fit type arrangement and, for simplicity, could be achieved in substantially the same way as for the first cap and body shoulders described above. Alternatively a different arrangement could be used.

One-way snap-fit type couplings provide the required functionality while remaining relatively easy to implement and design. The required features for such couplings can also be readily created by moulding, for example by injection moulding a plastic.

The first cap shoulder and the second cap shoulder carried by the cap may be provided by the same cap shoulder as this reduces the number of features that are required to be carried by cap. The first and second body shoulders carried by the body may be aligned on the body substantially parallel with the first axis. It should be understood that in an alternative embodiment the first body shoulder and the second body shoulder carried by the body may be provided by the same shoulder.

The, or each, displaceable shoulder may be carried on a respective movable arm as this is a convenient way to provide a shoulder which is displaceable. It should be understood that there are other ways in which a displaceable shoulder could be provided, although some may require potentially complex linkages. A movable arm can be created reasonably easily by providing an arm of a resiliently deformable material with a free end on which is mounted the shoulder and a tethered, or fixed, end which is attached to the body or cap. The attachment could be by integral moulding with the body or cap. The, or each, movable arm may form part of the body.

Each cap and body shoulder may be arranged so that it extends substantially perpendicular to the first axis as this provides reliable engagement between the surfaces and reduces the likelihood of slippage and/or resulting forces being generated.

At least one, or possibly each, body and cap shoulder may include a ramp extending from an edge of the shoulder towards a wall from which the shoulder projects to cause displacement of the displaceable shoulder during insertion of the body into the cap through contact of one shoulder with the ramp. Shoulder to ramp contact is achieved as the body is inserted into the socket of the cap and the shoulders approach one another. As the ramp makes contact with the shoulder a resulting force is generated. The resulting force causes the displaceable shoulder to move from its rest position so that the shoulders can pass one another. Once the shoulders have moved past one another the displaceable shoulder returns to the rest position. For example one the second body and cap shoulders have passed one another and returned to their rest position, the pre lock is engaged as any withdrawing of the body from the cap would result in shoulder to shoulder contact resisting said withdrawal.

The pre-lock further may further comprise a barrier in the direction of movement of the body into the socket, the barrier cooperating with at least one of the second cap or body shoulders to hinder movement of the body into the socket until a threshold force is exceeded. The barrier may be carried by the cap and may comprise a ridge extending from the cap.

In order to pass the barrier the at least one cap or body second shoulder that is resiliently displaceable from a rest position may have to be displaced. The force required to displace said second cap or body shoulder may determine the threshold force. The threshold force required to overcome the resistance provided by the barrier may be greater than a threshold force required to engage the pre-lock as this helps to avoid accidental passing of the barrier during pre-lock engagement. This could be achieved by requiring a greater displacement to pass the barrier than the shoulder of the pre-lock, or could be achieved by facilitating displacement of the shoulder prior to engagement of the pre-lock, for example using ramps or other means. The ridge that provides the barrier may extend perpendicular to the first axis. The ridge that provides the barrier may include no ramp associated therewith as this will increase the force required to pass the barrier.

Once past the barrier, there may be substantially no hindrance in the movement of the body within the socket created by interaction of the body with the socket. The cap may include a recessed region within which the cap shoulder can travel. The cap shoulder and/or the barrier may be arranged within, or extend into, that recess. The recess may extend substantially parallel with the first axis.

The cap may include at least two finger flanges which extend away from opposing sides of the cap. Such finger flanges can help a user apply an insertion force to the nasal spray assembly using only one hand. The flange surfaces may extend substantially perpendicular to the first axis so that the insertion force can be readily applied along said axis.

Each finger flange may be supported by at least one buttress extending between the flange and the cap. The, or each, buttress may extend substantially parallel with the first axis. The use of buttresses allows thinner, and therefore lighter, finger flanges to be provided while the buttress can provide the required mechanical stability.

The cap may include at least one opening into the socket and may include two openings into the socket on opposing sides of the cap. If the cap includes a pair of finger flanges which extend away from the cap on opposing sides, the openings may be provided between the finger flanges.

By providing at least one opening into the socket through the cap the possibility of the body and cap compressing a gas that may be within the socket and hindering insertion of the body into the cap is greatly reduced. By arranging the openings between the finger flanges the chances of a user accidentally covering one, or both, openings is reduced and this can help to provide a consistent user experience as the required insertion force is less likely to change between devices.

The cap and body may be fabricated from any suitable material, but a plastic material is particularly suitable. The piercing element may be made from a metal, for example a steel such as a stainless steel, to reduce the chances that the piercing element might bend or break in use. The piercing element may also include a sharpened end to facilitate piercing of the piston and a metal piercing element may be easier to sharpen. The piercing element may be a hollow needle.

The present invention also provides a nasal device comprising a body and a cap, the cap defining a socket into which the body can be inserted, an outlet and a piercing element, the piercing element including a piercer inlet and extending into the socket from a shoulder within the socket, the piercer inlet being connected to the outlet by a conduit, the nasal device being characterised in that the body and cap cooperate to provide a pre-lock and a post-lock, the pre-lock engages automatically when the body is inserted a first predetermined distance into the socket and, when engaged, the pre-lock substantially prevents withdrawal of the body from the cap and hinders further movement of the body into the cap until at least a threshold force has been applied thereby retaining the body and cap in a pre-use configuration, the post-lock engages automatically when the body is inserted a second predetermined distance into the socket and, when engaged, substantially prevents withdrawal of the body from the cap thereby substantially retaining the body and cap in a post-use configuration, the second predetermined distance is greater than the first predetermined distance, the nasal device being suitable for use in a nasal spray assembly as described above.

The present invention further provides a method of using a nasal spray assembly comprising a nasal device and a container, the nasal spray assembly being as described above, the method comprising the steps of:
a) arranging the container in the body;
b) inserting the body into the socket of the cap by a first distance to engage the pre-lock; and
c) applying a force exceeding a threshold force to insert the body into the socket by a second predetermined distance, thereby ejecting the medicament from the reservoir.

The nasal device would typically be supplied to a user in a pre-dose configuration in which the container is already located within the device and the pre-lock engaged. The use of an easy to engage pre-lock which includes an actuation threshold allows for simple assembly by, for example, a pharmaceutical manufacturer who may obtain the nasal device from a supplier and then assemble the final drug product into the device.

To use the device a user would typically put their first two fingers on the finger flanges and a thumb on a base of the body so that an insertion force can be applied to the body to insert the body into the cap. The user would then increase the insertion force applied until the threshold force is exceeded and the pre-lock allows further insertion of the body into the cap.

The threshold force to pass the pre-lock may be larger than the force required to insert the body into the cap once the pre-lock is passed and therefore the user may, having built up an insertion force greater than the threshold, naturally continue to insert the body until the post-lock is reached and engaged. This causes a substantially complete ejection of the reservoir from the outlet, or at least the ejection of at least a pre-determined volume therefrom and also ensures that the post-lock is engaged.

Once the post-lock is engaged the user cannot withdraw the body from the cap beyond the post-lock and the nasal device is retained in a post-use configuration in which it is clear that use has occurred. This means that the chance of a user believing that a device after use contains the required medicament is reduced. The post-lock also retains the nasal device is a post-use configuration which is typically more compact that the pre-use configuration which reduces waste volume.

The present invention also provides a nasal spray assembly comprising a nasal device and a container, the container including a reservoir containing a medicament, the reservoir being sealed by a movable piston, the nasal spray assembly being for administering the medicament to the nose of a user, the nasal device comprising a body and a cap, the cap defining a socket into which the body can be inserted, an outlet and a piercing element, the piercing element including a piercer inlet and extending into the socket from a piercer stop within the socket, the piercer inlet being connected to the outlet by a conduit, the body holding the container, and the nasal spray assembly being arranged such that, as the body is moved into the socket along a first axis, the piercing element pierces and passes through the piston such that the piercer inlet lies within the reservoir, contact between the piercer stop and piston causes the piston to be forced into the container, reducing the reservoir volume and thereby forcing medicament from the reservoir through the conduit and out of the outlet, the nasal spray assembly being characterised in that the body and cap cooperate to provide a pre-lock and a post-lock, the pre-lock engages automatically when the body is inserted a first predetermined distance into the socket and, when engaged, the pre-lock substantially prevents withdrawal of the body from the cap and hinders further movement of the body into the cap until at least a threshold force has been applied thereby retaining the body and cap in a pre-use configuration, the post-lock engages automatically when the body is inserted a second predetermined distance into the socket and, when engaged, substantially prevents withdrawal of the body from the cap thereby substantially retaining the body and cap in a post-use configuration, the second predetermined distance is greater than the first predetermined distance; and the medicament comprising one or more active pharmaceutical ingredient with pharmaceutically acceptable excipients suitable for nasal delivery.

The present invention further provides a method of delivering a medicament to the nose of a patient, the method comprising the steps of:
a) providing a nasal spray assembly substantially as described above, the pre lock being engaged;
b) arranging the outlet of the device in or near the nostril of a user; and
c) applying a force exceeding a threshold force to insert the body into the socket by a second predetermined distance, thereby ejecting the medicament from the reservoir from the outlet and engaging the post-lock.

A nasal spray assembly according to the present invention can be used to delivery any medicament that can be formulated in a manner suitable to flow from the container when then reservoir volume is reduced. A suitable formulation might be a liquid, gas or a powder. A liquid formulation might be a solution, suspension, pure liquid or a combination.

Suitable medicaments that can be formulated in one or more of the above mentioned forms may comprise one or more active ingredients from the class of serotonergics ($5-HT_1$, $5-HT_2$, $5-HT_3$, $5-HT_4$, $5-HT_5$, $5-HT_6$, $5-HT_7$ agonists & antagonists), selective serotonin reuptake inhibitors (SSRIs), Serotonin-norepinephrine reuptake inhibitors (SNRIs), Serotonin-norepinephrine-dopamine reuptake inhibitors (SNDRIs), antidepressants, ergolines, calcium channel blockers, corticosteroids, sympatholytics, anticonvulsants, antipsychotics (such as those referred to in US20060039869); opioid agonists and antagonists (such as those referred to in US20150258019); sedatives, anti-seizure drugs and opiates (such as those referred to in WO2012119153); vasodilators (such as those referred to in US20150005356); and other classes of drugs (including, cannabinoids, analgesic agents, such as NSAIDs, and drugs for the treatment of Parkinson's disease, but also drugs where rapid onset of action may be required, such as drugs for the treatment of nausea and vertigo, convulsions, panic attacks, cardiac problems, impotence, erectile dysfunction, migraine, sedation (particularly in children) and withdrawal symptoms. Suitable drugs may also include benzodiazepines, midazolam, diazepam and diamorphine).

The above referenced one or more active ingredients would not only include their base compound(s) per se but would also envisage their respective pharmaceutically acceptable salts, pharmaceutically acceptable solvates, pharmaceutically acceptable hydrates, pharmaceutically acceptable enantiomers, pharmaceutically acceptable esters, pharmaceutically acceptable polymorphs, pharmaceutically acceptable prodrugs, pharmaceutically acceptable complexes etc.

It will further be understood that any given medicament comprising one or more of the above active ingredients along with pharmaceutically acceptable excipients may be administered by means of the nasal spray assembly as envisaged under the present invention, and the specific dose level and frequency of dosage of the medicament for any particular patient may be varied and will depend upon a variety of factors including the activity of the specific active ingredient employed, the metabolic stability and length of action of that active ingredient, the patient's age, body weight, general health, sex and diet, the mode and time of administration, the rate of excretion, the drug combination, the severity of the particular condition, and the host undergoing therapy.

Figure 1:
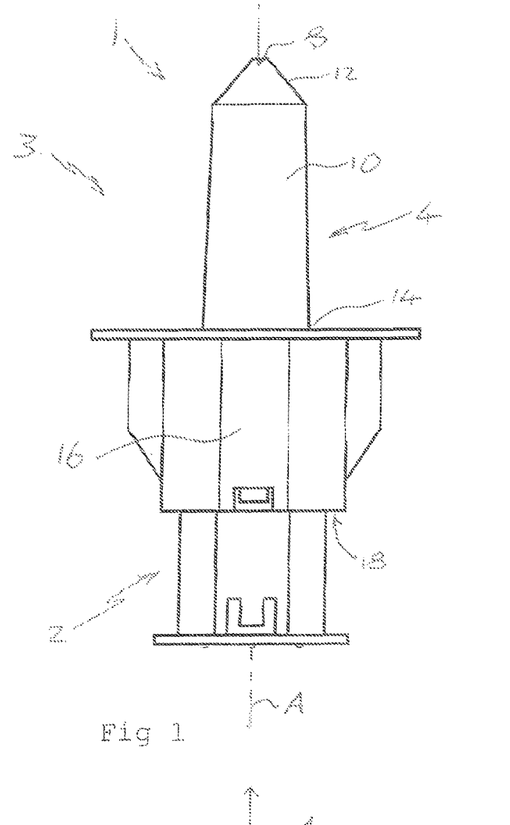
FIG. 1 shows a schematic view from the front of a nasal spray assembly in a pre-use configuration.

In the following sections, the invention is described with reference to the figures. FIG. 1 shows a schematic view from the front of a nasal spray assembly 1 in a pre-use configuration. The nasal spray assembly 1 comprises a nasal device 3, comprising a body 2 and a cap 4.

Figure 2:
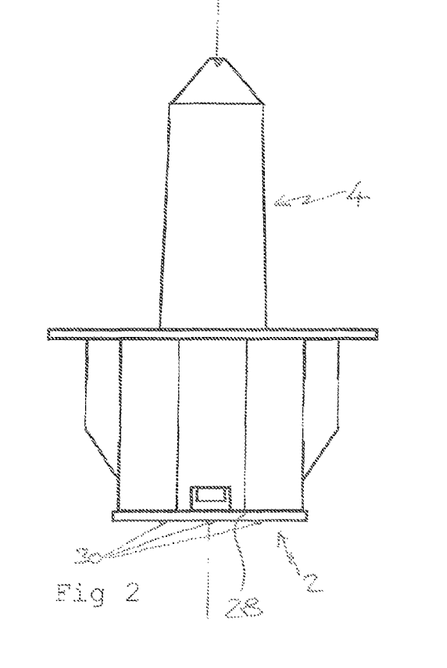
FIG. 2 shows a schematic view from the front of a nasal spray assembly in a post-use configuration.

FIG. 2 shows the nasal spray assembly 1 of FIG. 1 in a post use configuration in which the body 2 has been inserted into the cap 4 such that only an endplate 28 of the body is visible. The endplate 28 includes surface projections 30 to increase the grip of the surface for the finger of a user. The body 2 is inserted into the cap substantially along a first axis A.

Figure 9:
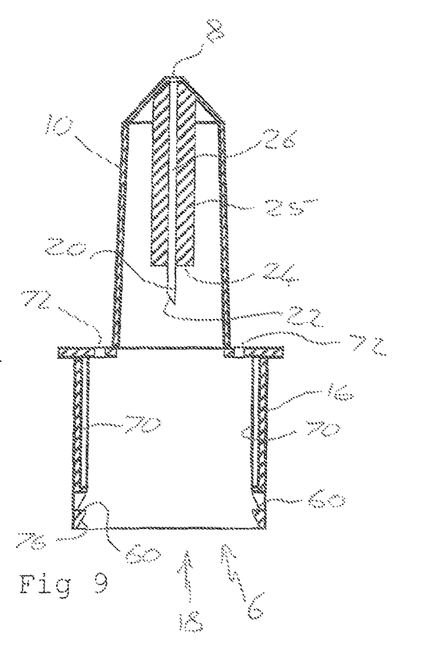
FIG. 9 shows a schematic cross section view from the side of a cap of the nasal device of FIG. 1.

Referring also to FIG. 9, the cap 4 defines a socket 6 into which the body 2 can be inserted. The cap 4 includes an outlet 8 at an outlet end 12 of a nostril portion 10 which is shaped for insertion into the nostril of a user. A base end 14 of the nostril portion 10 being connected to a base portion 16 of the cap 4 which includes the opening 18 of the socket 6. The nostril portion 10 of the cap includes a piercing element 20 (best seen in FIG. 9). The piercing element 20 includes a piercer inlet 22 and extends into the socket 6 from a piercer stop 24 of a holder 25 for the piercer element within the socket 6. The piercer inlet 22 is connected to the outlet 8 by a conduit 26.

Figure 3:
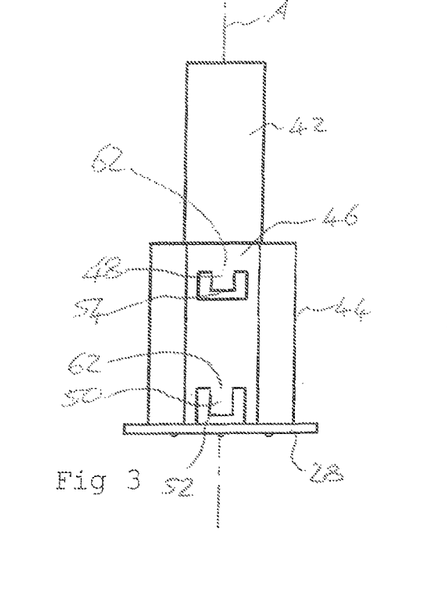
FIG. 3 shows a schematic view from the front of a body of the nasal device of FIG. 1.

FIG. 3 shows a schematic view from the front of a body 2 of the nasal device 3 of FIG. 1. The body 2 comprises tower 42 within which a container 32 can be held. The tower 42 extends from the endplate 28 and is surrounded adjacent the endplate 28 by a peripheral wall 44. The peripheral wall 44 is spaced apart from, and completely surrounds a base of the tower 42. The tower 42 and peripheral wall 44 extend from the endplate 28 substantially parallel with the first axis A. The peripheral wall 44 extends from the endplate 28 to between about 30% and 70% of the height of the tower 42.

The peripheral wall 44 also includes a facet 46 which cooperates with the socket 6 to rotationally align the cap 4 and body 2 about the first axis A. The peripheral wall also includes a first movable arm 50 and a second movable arm 48. The first movable arm 50 carries a first displaceable body shoulder 52 and the second movable 48 arm carries a second displaceable body shoulder 54. The movable arms 48,50 are defined by substantially 'U' shaped cut-outs through the peripheral wall 44. Each movable arm 48,50 is coupled to the peripheral wall 44 at a fixed end 62.

Figure 4:
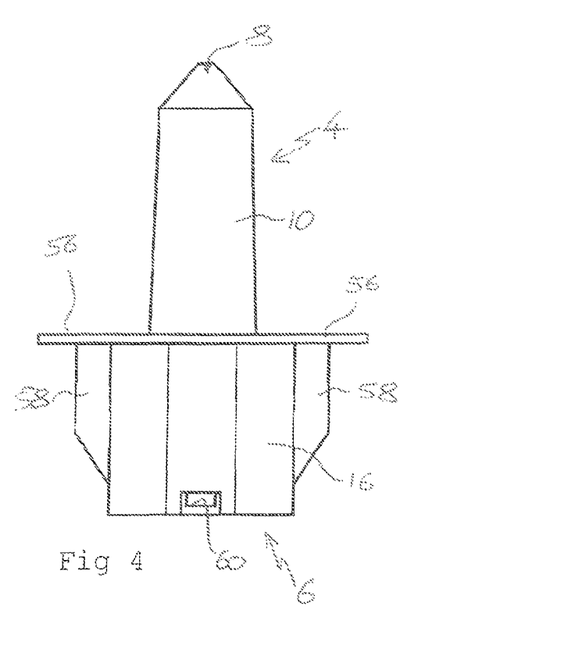
FIG. 4 shows a schematic view from the front of a cap of the nasal device of FIG. 1.
Figure 6:
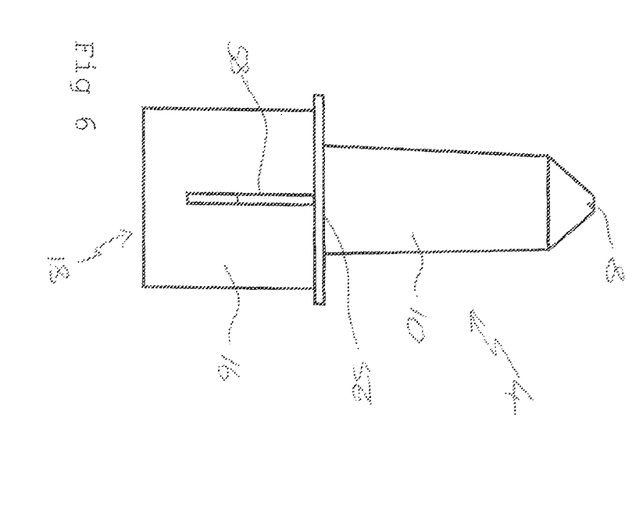
FIG. 6 shows a schematic view from the side of a cap of the nasal device of FIG. 1.

FIGS. 4 and 6 show a schematic view from the front and side respectively of a cap 4 of the nasal device 3 of FIG. 1. The cap 4 includes two finger flanges 56 which extend from opposing sides of the cap 4 perpendicular to the first axis A from a position between the nostril portion 10 and the base portion 16. The finger flanges 56 are supported by buttresses 58 which extend from the finger flanges 56 to the base portion 16 of the cap 4. The buttresses extend substantially parallel with the first axis A.

The cap 4 also includes a cap shoulder 60 adjacent the opening 18 into the socket 6 which will, in use, engage with the body shoulders 52,54 of the body. The cap shoulder 60 is arranged substantially equidistant from both buttresses 58.

Figure 5:
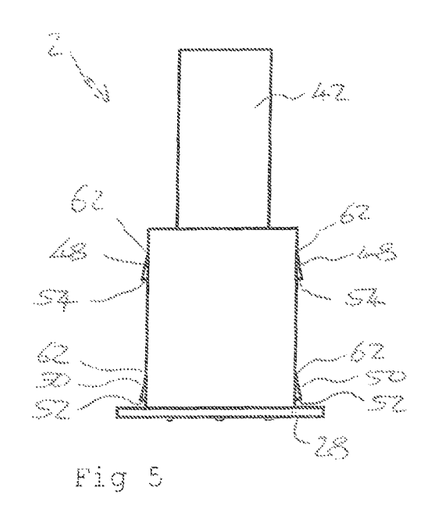
FIG. 5 shows a schematic view from the side of a body of the nasal device of FIG. 1.

FIG. 5 shows a schematic view from the side of a body 2 of the nasal device 3 of FIG. 1. From this figure it can be more easily seen that the peripheral wall 44 carries pairs of movable arms 48, 50 arranged on opposing sides of body 2.

Figure 7:
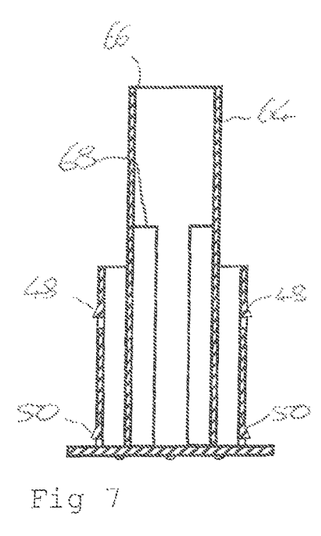
FIG. 7 shows a schematic cross section view from the side of a body of the nasal device of FIG. 1.
Figure 8:
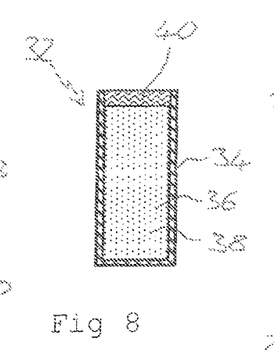
FIG. 8 shows a schematic cross section view of a container for use with the nasal device of FIG. 1.

FIGS. 7, 8 and 9 show schematic cross section views of the body 2, container 32 and cap 4 respectively.

In FIG. 7 it can be seen that the tower 42 is provided by a cylindrical wall 64 which is open at a top end 66. Within the tower there is a stop 68 such that when the container 32 is inserted into the open end 66 it will rest on the stop 68. The container 32 may include a shoulder, flange or other feature at one end to prevent the container 32 being inserted into the tower 42 incorrectly (upside-down).

FIG. 8 shows a schematic cross section view of a container 32 for use with the nasal device of FIG. 1. The container 32 comprises housing 34 within which is located a reservoir 36 containing a medicament, in this case a fluid 38. The housing is open at one end and the reservoir 36 is sealed by a movable piston 40.

FIG. 9 shows a schematic cross section view from the side of a cap 4 of the nasal device 3 of FIG. 1. The cap shoulder 60 of the base portion 16 of the cap 4 can also be more clearly seen. A recess 70 extending substantially parallel with the first axis A is provided in the socket 6 in which the body shoulders 52, 54 of the body 2 will slide in use so that they are substantially in their rest position.

Openings 72 through the finger flanges 56 and into the socket 6 are also shown in this figure.

Figures 10, 11:
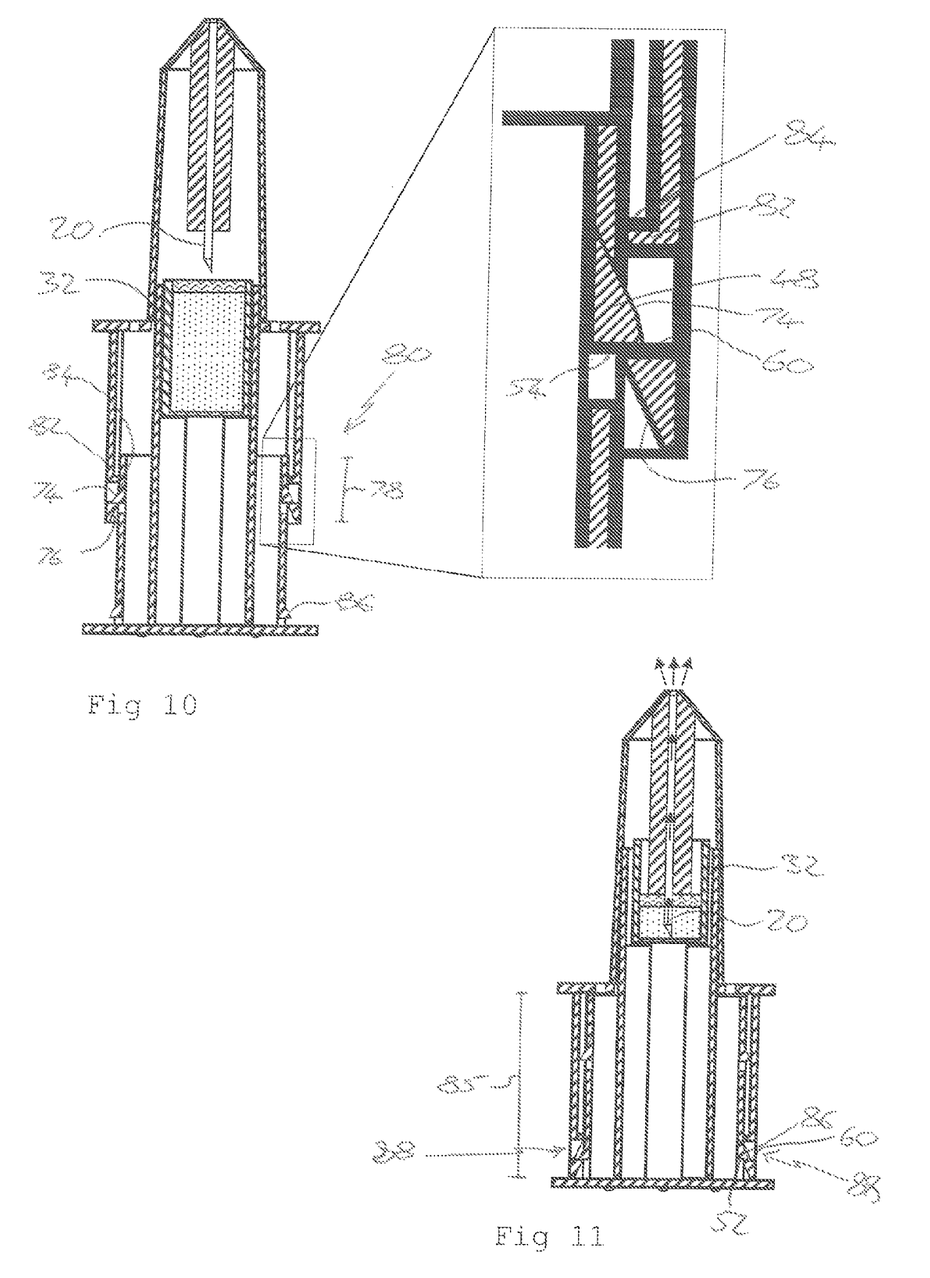
FIG. 10 shows a schematic cross section view from the front of a nasal spray assembly in a pre-use configuration.
FIG. 11 shows a schematic cross section view from the front of a nasal spray assembly in a post-use configuration.

FIGS. 10 and 11 show the operation of the nasal spray assembly 1 in more detail and the method of operation will now be described with reference to these Figures.

The container 32 is loaded into the tower 42 of the body 2 and the body is inserted into the socket 6 of the cap 4 along the first axis A. The peripheral wall 44 of the body 2 cooperates with the socket 6 to rotationally align the body 2 and the cap 4 about the first axis so that the body shoulders 52,54 of the body 2 and the cap shoulder 60 of the cap 4 are aligned along the first axis A. It will be understood that the cap could include two separate cap shoulders and provide the same functionality, but it is more efficient to have the same cap shoulder 60 of the cap used for both the pre and post locks.

Each of the shoulders 54, 60 is preceded in the direction of relative travel during insertion by a ramp 74, 76 respectively. Once aligned about the first axis A, the body 2 is inserted into the cap 4 along the first axis until the ramps 74, 76 make contact. Further insertion of the body 2 is made possible by the displacement of the body shoulder 54. The displacement results from the resilient deformation of the movable arm 48, which carries the body shoulder 54, and is caused by the ramps sliding past one another.

Once the body 2 has travelled a first pre-determined distance 78 into the socket 6, shoulder 54 moves beyond the cap shoulder 60 in the direction of insertion and the resiliently deformable arm 48 returns to its rest position and the engagement of the body and cap shoulders 54 and 60 substantially prevent withdrawal. The body and cap shoulders 54 and 60 therefore combine to provide a first function of the pre-lock 80 which automatically engages.

In this pre-use configuration as shown in FIG. 10 the pre-lock 80 is engaged. The pre-lock further comprises barrier 82, in this case a ridge 84 in the cap 4 projecting into the recess 70 beyond the cap shoulder 60 in the direction of insertion. The ridge 84 and ramp 74 of the second movable arm 48 interact as set out for the interaction of the second movable arm 48 and the cap shoulder 60, except that the ridge 84 does not include a preceding ramp and therefore the insertion force required to move the second shoulder 54 beyond the ridge 84 is higher than the force required to move it past the shoulder 60. This provides a threshold force that prevents further insertion and this force can be varied by altering the size of the ridge 84 in a direction perpendicular to the first axis A.

In the pre-use configuration the piercing element 20 has not pierced the piston 40 and the device is ready for use by a user.

During use an insertion force above the threshold force is applied to the body 2 and the second body shoulder 54 of the body moves past the ridge 84. The moveable arm 48 is then able to return to its rest position as the body shoulder 54 fits within the recess 70 and therefore the body 2 is able to slide within the cap 4 without hindrance from the body shoulders 54.

As the body 2 is inserted further, the piercing element 20 contacts and then pierces the piston 40 so that the piercer inlet 22 is within the reservoir 36 and further movement brings the piercer stop 24 of the piercing element into contact with the piston 40. Once contact between the piercer stop 24 and the piston 40 is established, further insertion of the body 2 moves the piston 40 to reduce the volume of the reservoir 36 which expels the fluid 38 through the outlet 8 via the conduit 26.

During insertion of the body 2 into the cap 4, air trapped within the socket may be expelled through the openings 72 to prevent compression of said air which may alter the insertion force required.

When the body has almost been inserted a second predetermined distance 85 a ramp 86 which precedes the first body shoulder 52 makes contact with the ramp 76 of the cap shoulder 60 of the cap 4. The interaction of the ramps 86 and 76 is substantially as described above and when the body 2 is inserted a second predetermined distance 85 the first body shoulder 52 has moved beyond the cap shoulder 60 and returned to a rest position thereby preventing withdrawal of the body 2 from the cap 4. Further movement of the body 2 into the cap 4 may be prevented by the endplate 28, or by contact of the peripheral wall 44 with the cap 4. The first body shoulder 52 and the cap shoulder 60 therefore provide an automatically engaging post-lock 88 which retains the nasal device in a post use configuration as shown in FIG. 11.

A particularly suitable medicament for delivery by use of the device assembly of the present invention is solution of Zolmitriptan, and that the following example is for the purpose of illustration only and is not intended in any way to limit the scope of the present invention.

Example

A formulation suitable for delivery by the nasal spray assembly can be made as follows:

| Sr. No. | Ingredient | Quantity (% w/w) |
| --- | --- | --- |
| 1 | Zolmitriptan | 5.00% |
| 2 | Citric acid anhydrous | 2.60% |
| 3 | Anhydrous disodium hydrogen phosphate | 1.50% |
| 4 | Purified water | q.s. to 100 ml |

Manufacturing Process:
1. A volume of freshly prepared purified water was transferred in a suitable vessel under continuous nitrogen sparging.
2. Citric acid anhydrous was added and dissolved under continuous nitrogen sparging.
3. Zolmitriptan was added and dissolved while stirring with nitrogen sparging to obtain a clear colourless to pale yellow solution.
4. Anhydrous disodium hydrogen phosphate was added and dissolved while stirring under continuous nitrogen sparging followed by make-up of the volume to specification with purified water.
5. pH checked followed by aseptic filtration of the solution with 0.22 micron filter
6. Solution filled and packed in suitable glass containers closed with a rubber piston.

It will be readily apparent to one skilled in the art that varying substitutions and modifications may be made to the invention disclosed herein without departing from the spirit of the invention. Thus, it should be understood that although the present invention has been specifically disclosed by the preferred embodiments and optional features, modification and variation of the concepts herein disclosed may be resorted to by those skilled in the art, and such modifications and variations are considered to be falling within the scope of the invention.

It is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It must be noted that, as used in this specification and the appended claims, the singular forms "a," "an" and "the" include plural references unless the context clearly dictates otherwise. Thus, for example, reference to "excipient" includes a single excipient as well as two or more different excipients; reference to an "active ingredient" refers to a single active ingredient or to combinations of two or more active ingredients, and the like.

The invention claimed is:

1. A nasal spray assembly configured for administering a medicament to the nose of a user, comprising:
   a nasal device including a body and a cap; and
   a container including a reservoir containing a medicament, the reservoir being sealed by a movable piston, wherein:
   the body holds the container,
   the cap defines a socket for receiving the body, an outlet and a piercing element, the piercing element including a piercer inlet and extending into the socket from a piercer stop within the socket, the piercer inlet being connected to the outlet by a conduit,
   the cap includes finger flanges that extend away from opposing sides of the cap, the finger flanges defining respective flange surfaces that are substantially perpendicular to a first axis, and the cap including two openings between the finger flanges,
   the nasal spray assembly is arranged such that, as the body is moved into the socket along the first axis, the piercing element pierces and passes through the movable piston such that the piercer inlet lies within the reservoir, contact between the piercer stop and piston causes the movable piston to be forced into the container, reducing a reservoir volume and thereby forcing medicament from the reservoir through the conduit and out of the outlet,
   the body and cap cooperate to provide a pre-lock and a post-lock,
   the pre-lock engages automatically when the body is inserted a first predetermined distance into the socket and, when engaged, the pre-lock substantially prevents withdrawal of the body from the cap and hinders further movement of the body into the cap until at least a threshold force has been applied thereby retaining the body and cap in a pre-use configuration,
   the post-lock engages automatically when the body is inserted a second predetermined distance into the socket and, when engaged, substantially prevents withdrawal of the body from the cap thereby substantially retaining the body and cap in a post-use configuration, and
   the second predetermined distance is greater than the first predetermined distance.

2. The nasal spray assembly as claimed in claim 1, in which the pre-lock or the post-lock comprises a first cap shoulder carried by the cap and a first body shoulder carried by the body, at least one of the first cap shoulder and first body shoulder being resiliently displaceable from a rest position to move past the other as the body enters the cap and the first cap shoulder and the first body shoulder cooperating in the rest position to substantially prevent withdrawal of the body from the cap.

3. The nasal spray assembly as claimed in claim 2, in which the post lock comprises the first cap shoulder and the first body shoulder and the pre-lock comprises a second cap shoulder carried by the cap and a second body shoulder carried by the body, at least one of the second cap shoulder and the second body shoulder being resiliently displaceable from a rest position to move past the other as the body enters the cap and the second cap shoulder and the second body shoulder cooperating in the rest position to substantially prevent withdrawal of the body from the cap.

4. The nasal spray assembly as claimed in claim 3, in which the first cap shoulder and the second cap shoulder carried by the cap are provided by a single cap shoulder and the first body shoulder and second body shoulder carried by the body are aligned on the body along the first axis.

5. The nasal spray assembly as claimed in claim 3, in which each of the first cap shoulder, the second cap shoulder, the first body shoulder and the second body shoulder is carried on a respective movable arm.

6. The nasal spray assembly as claimed in claim 5, in which each movable arm associated with the first body shoulder and the second body shoulder forms part of the body.

7. The nasal spray assembly as claimed in claim 3, in which each of the first cap shoulder, the second cap shoulder, the first body shoulder and the second body shoulder extends substantially perpendicular to the first axis.

8. The nasal spray assembly as claimed in claim 7, in which each of the first cap shoulder, the second cap shoulder, the first body shoulder and the second body shoulder includes a ramp extending from an edge of each of the shoulders and towards a wall from which the respective shoulder projects to cause displacement of the respective shoulder during insertion of the body into the cap through ramp-to-ramp contact.

9. The nasal spray assembly as claimed in claim 3, in which the pre-lock further comprises a barrier in the direction of movement of the body into the socket, wherein the barrier together with at least one of the second cap shoulder and second body shoulder hinders movement of the body into the socket until a threshold force is exceeded.

10. The nasal spray assembly as claimed in claim 9, in which the barrier is carried by the cap.

11. The nasal spray assembly as claimed in claim 10, wherein the barrier is provided by a ridge in the cap, the ridge projecting into a recess beyond the cap shoulder in the direction of insertion, and the ridge not including a preceding ramp.

12. The nasal spray assembly as claimed in claim 9, wherein the threshold force is the force required to displace at least one of the second cap shoulder and the second body shoulder from a rest position to thereby pass the barrier.

13. The nasal spray assembly as claimed in claim 2, in which the cap includes a recess within which each of the first body shoulder and the second body shoulder carried by the body is intended to travel.

14. The nasal spray assembly as claimed in claim 1, in which each finger flange is supported by a respective buttress, the buttresses extending between the finger flange and the cap, wherein each buttress of the buttresses extends substantially parallel with the first axis.

15. The nasal spray assembly as claimed in claim 1, wherein the cap and body are fabricated from plastic with the exception of the piercing element which is fabricated from metal.

16. The nasal spray assembly as claimed in claim 1, wherein the medicament is suitable for nasal delivery and comprises one or more active pharmaceutical ingredient with one or more pharmaceutically acceptable excipient.

17. A method of using the nasal spray assembly of claim 1, the method comprising:
a) arranging the container in the body;
b) inserting the body into the socket of the cap by a first distance to engage the pre-lock; and
c) applying a force exceeding a threshold force to insert the body into the socket by a second predetermined distance, thereby ejecting the medicament from the reservoir from the outlet and engaging the post-lock.

18. A nasal device comprising:
a body;
a cap that defines a socket into which the body can be inserted;
an outlet; and
a piercing element that includes a piercer inlet and extends into the socket from a shoulder within the socket, the piercer inlet being connected to the outlet by a conduit, wherein:
the cap includes finger flanges that extend away from opposing sides of the cap, the finger flanges defining respective flange surfaces that are substantially perpendicular to a first axis, and the cap including two openings between the finger flanges,
the body and cap cooperate to provide a pre-lock and a post-lock,
the pre-lock engages automatically when the body is inserted a first predetermined distance into the socket and, when engaged, the pre-lock substantially prevents withdrawal of the body from the cap and hinders further movement of the body into the cap until at least a threshold force has been applied thereby retaining the body and cap in a pre-use configuration,
the post-lock engages automatically when the body is inserted a second predetermined distance into the socket and, when engaged, substantially prevents withdrawal of the body from the cap thereby substantially retaining the body and cap in a post-use configuration, and
the second predetermined distance is greater than the first predetermined distance.

* * * * *